United States Patent [19]

Bombardelli

[11] Patent Number: 5,917,062
[45] Date of Patent: Jun. 29, 1999

[54] INTERMEDIATES AND METHODS USEFUL IN THE SEMISYNTHESIS OF PACLITAXEL AND ANALOGS

[75] Inventor: Ezio Bombardelli, Milan, Italy

[73] Assignee: Indena S.p.A, Milan, Italy

[21] Appl. No.: 08/975,804

[22] Filed: Nov. 21, 1997

[51] Int. Cl.$^6$ .................................................. C07D 305/14
[52] U.S. Cl. ........................................... 549/510; 549/511
[58] Field of Search ...................... 549/510, 511

[56] References Cited

U.S. PATENT DOCUMENTS

| | | | |
|---|---|---|---|
| Re. 34,277 | 6/1993 | Denis et al. | 549/510 |
| 4,814,470 | 3/1989 | Colin et al. | 514/449 |
| 4,857,653 | 8/1989 | Colin et al. | 549/511 |
| 4,924,011 | 5/1990 | Denis et al. | 549/510 |
| 5,175,315 | 12/1992 | Holton | 549/510 |
| 5,336,785 | 8/1994 | Holton | 549/214 |
| 5,470,866 | 11/1995 | Kingston et al. | 514/376 |
| 5,476,954 | 12/1995 | Bourzat et al. | 549/510 |
| 5,574,156 | 11/1996 | Holton | 540/357 |
| 5,578,739 | 11/1996 | Hittinger | 549/510 |
| 5,621,121 | 4/1997 | Commercon et al. | 549/510 |

FOREIGN PATENT DOCUMENTS

| | | |
|---|---|---|
| 0 253 738 | 1/1988 | European Pat. Off. . |
| 0 253 739 | 1/1988 | European Pat. Off. . |
| 0 400 971 | 5/1990 | European Pat. Off. . |
| 0 525 589 | 7/1992 | European Pat. Off. . |
| WO 96/36622 | 11/1996 | WIPO . |

*Primary Examiner*—Ba K. Trinh
*Attorney, Agent, or Firm*—Pennie & Edmonds LLP

[57] ABSTRACT

The semisynthesis of paclitaxel and its analogs using new intermediates which are derivatives of 10-deacetyl-baccatin III, as well as to a method for preparing these derivatives. These novel derivatives have alkyl carbonate or alkyl carbonyl substituents in the 7 position.

12 Claims, No Drawings

INTERMEDIATES AND METHODS USEFUL IN THE SEMISYNTHESIS OF PACLITAXEL AND ANALOGS

TECHNICAL FIELD

The present invention relates to semisynthes paclitaxel and its analogs using new intermediates which are derivatives of 10-deacetyl-baccatine III, as well as to a method for preparing these derivatives. These novel derivatives have carbonate substituents in the 7 position, such as t-butoxy-carbonate.

BACKGROUND ART

Paclitaxel, a well known potent antitumor compound having a broad spectrum of antitumor activities, has the following structure of formula (I):

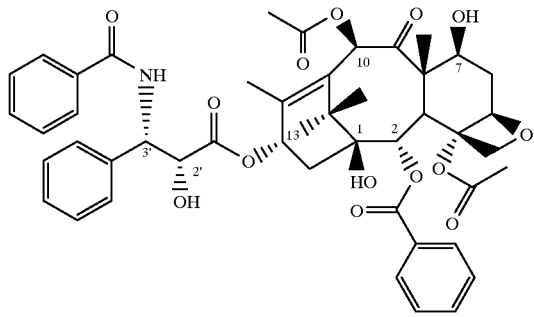

Commercial pharmaceutical products containing this compound are available, e.g., for treating ovarian and breast cancer in women. For these reasons, greater and greater supplies of this compound are required each year. Paclitaxel and baccatine III are extracted with difficulty and in general in low yields from the trunk barks of different Taxus species. Thus, alternative sources of this compound are necessary.

Several synthetic methods have been reported both in scientific and patent literature. U.S. Pat. No. RE-34,227 (a reissue of U.S. Pat. No. 4,924,011) discloses the semisynthesis of paclitaxel using a 10-deacetyl-baccatine III derivative which is protected in the 7 position with a tri-alkyl-silyl group which is specifically shown as a tri-ethyl-silyl ("TES") group and which is also protected in the 10 position with an acetyl group. This baccatine III derivative is allowed to react with a (2R,3S)-N-benzoyl-2-O-(1-ethoxyethyl)-3-phenylisoserine compound before removal of the protecting groups to obtain the paclitaxel.

In PCT application WO-93/06094, paclitaxel was prepared by reacting a side chain precursor of a β-lactam compound with 7-O-TES-baccatine III derivative to provide a 7-TES-baccatin III reaction product. After a mild acidic post-reaction treatment, paclitaxel was obtained.

In U.S. Pat. No. 5,476,954, the synthesis of paclitaxel was conducted starting from a protected 10-deacetyl-baccatine III derivative that contained a 2,2,2-tri-chloroethoxy-carbonyl ("TROC") protective group in both the 7 and 10 positions of the derivative.

It is well known that the key step in the semisynthesis of paclitaxel is to selectively protect the 7 position with a leaving group that can be easily removed. This is because the hydroxy group in that position of the taxane structure is much more reactive than those in position 10 or 13, and the paclitaxel product to be synthesized needs to have a hydroxy group in that position. Until now, however, the most useful protecting group was considered to be TES. The derivatization yield of 10-deacetyl-baccatine III with TES is typically about 85% when 20 moles of the reagent are used. The acetylation step, using 5 equivalents of acetylchloride, provides about 85% of 7-TES-baccatine III. as per the teachings of PCT application WO-93/06094 and its U.S. equivalent documents such as U.S. Pat. No. 5,574,156.

In view of the importance of paclitaxel, however, new and improved methods for its production are desirable. The present invention provides such improved syntheses of paclitaxel and its analogs primarily using new derivatives of 10-deacetyl-baccatin III as intermediates.

SUMMARY OF THE INVENTION

The present invention relates to an intermediate for use in the semisynthesis of paclitaxel, comprising a compound of formula (II):

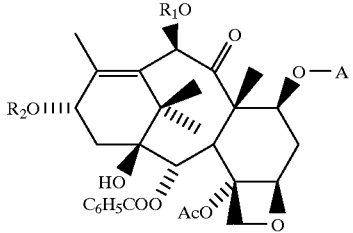

wherein:
A is

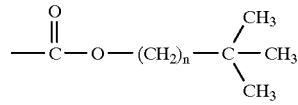

with n being an integer of 0 to 3, $R_1$ is a hydroxy-protecting group or a hydrogen atom; and $R_2$ is a hydroxy-protecting group or a hydrogen atom.

Preferably, $R_1$ is A, an acetyl group or a tri-alkylsylil group wherein each alkyl group contains 1 to 3 carbon atoms, $R_2$ is a (2R,3S)-3-phenylisoserine derivative having the structure:

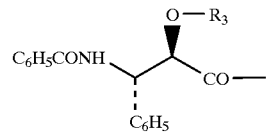

where $R_3$ is a hydroxy-protecting group, such as A; a methoxy methyl, 1-ethoxyethyl, benzyloxymethyl, (β-trialkyl-silylethoxy)methyl where each alkyl group contains 1 to 3 carbon atoms, tetrahydropyranyl or 2,2,2-trichloroethoxycarbonyl group; or a hydrogen atom.

The invention further relates to a process for producing paclitaxel by the steps of forming the intermediate compound of formula (II) and removing the A and $R_3$ groups to form paclitaxel. In this method, when n is 0, $R_1$ is an acetyl group, and $R_2$ is a (2R,3S)-3-phenylisoserine derivative having the structure:

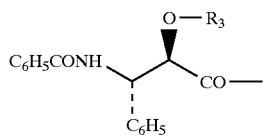

where $R_3$ is a hydrogen atom, the method further comprises forming the intermediate compound by reacting 10-deacetylbaccatine III with t-butoxy-pyrocarbonate to obtain 7-t-butoxy-carbonyl-10-deacetyl baccatine III; acetylating 7-t-butoxy-10-deacetyl baccatine III to obtain 7-t-butoxy-carbonyl-baccatine III and esterifying the hydroxy group in position 13 of the 7-t-butoxy-carbonyl-baccatine III with an oxazolidine derivative of formula (III):

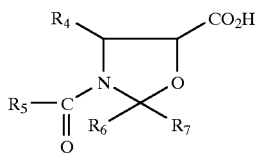

wherein $R_4$ is an aryl group or a straight or branched chain alkyl or alkenyl group having 1–5 carbon atoms; and $R_5$ is $R_4$ or a t-butoxy group, and each of $R_7$ and $R_8$ is a halogenated methyl group. Advantageously, an excess of the 7-t-butoxycarbonyl-baccatine III compound is used relative to the oxazolidine derivative.

Another intermediate for use in the semisynthesis of paclitaxel according to the present invention comprises the oxazolidine derivative of formula (III), where $R_4$, $R_5$, $R_6$ and $R_7$ are as defined above. Preferably, $R_4$ is phenyl, $R_5$ is phenyl or a t-butoxy group, and each of $R_6$ and $R_7$ is a $ClCH_2-$, $BrCH_2-$ or $F_3C-$ group.

DETAILED DESCRIPTION OF THE INVENTION

The semisynthesis of paclitaxel of the general formula (I) given above through the use of the new intermediates of formula (II). These new intermediates are key intermediate which also can be used for the semisynthesis of docetaxel and other analogs of paclitaxel. The process for their preparation is also described.

It has been found, surprisingly, that protecting the hydroxy group at position 7 of 10-deacetylbaccatine III or similar taxane derivatives with the same basic structure, with certain carbonate compounds provides enhancements in the preparation of paclitaxel from such derivatives.

A preferred protective group is t-butoxypyrocarbonate (BOC), although other carbonate groups having the structure

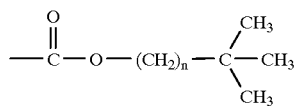

can be used. In this structure, n is an integer of 0 to 3, with n being 0 preferred. This protective group can be substituted in position 7 and, if desired, as well as in position 10.

As position 10 is not as reactive as position 7, a number of other protective groups can be used in position 10. In particular, the group $-OR_1$ can be used, where $R_1$ is a hydroxy-protecting group or a hydrogen atom. Any of a wide variety of hydroxy-protecting groups can be used, including the carbonate groups described above for A, the $G_1$ groups of the compounds of formula III of U.S. Pat. Nos. 5,578,739 or 5,621,121, the $R_2$ groups of the compounds of formula III of U.S. Pat. No. 5,476,954, or the $R_3$ substituents of the compounds of formula IV of U.S. Pat. No. Re. 34,277.

It is possible to obtain almost quantitative yields of the 7-BOC-10-deacetylbaccatine III derivative from 10-deacetylbaccatine III. The use of BOC as a protecting group for alcohols was not previously reported before in literature, and particularly on taxane structures. This group is easily and selectively removed in very mild acidic conditions using a catalytic amount of mineral or organic acids, preferably formic or F3C—COOH.

The synthesis of 7-BOC-10-deacetylbaccatine III or its analog is performed in chlorinated solvents, preferably in methylene chloride using dimethylformamide as a cosolvent. 1 Mole of 10-deacetyl-baccatine III or the chosen taxane analog is reacted with 1.2 to 2.5 equivalents t-terbutoxy-pyrocarbonate in the presence of 1.2 equivalents of ethyldiisopropylamine and a catalytic amount of 4-dimethylaminopyridine. Under these conditions, it is possible to obtain in almost quantitative yields the 7-BOC-derivative. This compound can be converted into 7-BOC-10-acetyl derivative using acetyl chloride, bromide or diketene as shown in the examples.

These derivatives can be converted to biologically active compounds by esterifying the hydroxy group at the 13 position with an oxazolidine derivative of formula (III):

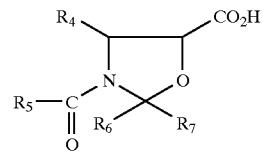

wherein $R_4$ is an aryl group or a straight or branched chain alkyl or alkenyl group having 1–5 carbon atoms; and $R_5$ is $R_4$ or a t-butoxy group, and each of $R_6$ and $R_7$ is a halogenated methyl group.

The reaction is performed in aprotic solvents, preferably benzene, toluene, xylene, chlorobenzene or ethylbenzene in the presence of dicycloecxylcarbodiimmide (DCC) and a catalytic amount of dialkylamino pyridine, preferably 4-dimethylaminopyridine at temperatures ranging from about 50° C. to 100° C., and preferably 70° C.

Preferably, to obtain the desired compounds, 4 Moles of condensing agent and 1.5 Mole of the oxazolidine derivative are used for 1 Mole of protected taxane. After elimination of the reaction byproducts and the solvent the ester at position 13 is isolated in crude form. This compound is treated in methanol with a catalytic amount of anhydrous HCl at room temperature or at temperatures ranging from about 5° C. to 10° C., and preferably at 0° C., with concentrated formic acid (98%) until complete deprotection of the BOC group at the 7 position and the protective group $R_3$ of the side chain at position 13 is achieved. After treatment of the reaction mixture with brine, the taxane derivative is extracted with a solvent that is non-miscible with water, and preferably with ethylacetate. After distillation of the extraction solvent, the taxane derivatives are directly crystallized with suitable solvents or submitted to chromatographic process using silica-gel and as eluting solvents, a mixture preferably constituted by exane/ethylacetate in a suitable range.

Alternatively, paclitaxel and its analogs can be prepared by esterifying the protected baccatine with a phenylisoserine chain esterified at 2 position with BOC. The reaction conditions are those above described for the oxazolidine derivatives.

The hydroxy group at position 13 can be esterified in a number of other ways as disclosed, e.g., in U.S. Pat. Nos. 5,578,739, 5,574,156, 5,621,121, 5,476,954, 5,470,866, 4,857,653, 4,814,470, and Re. 34,277, and in European Patent Application 0,525,589-A1. To the extent necessary to understand the present invention, all patents cited in the detailed description of this specification are expressly incorporated by reference herein.

EXAMPLES

The examples below are reported, without implied limitation, to show how the invention can be put in practice.

EXAMPLE 1

Synthesis of 7-BOC-10-deacetylbaccatine III

A 500 mg sample of 10-deacetylbaccatine III (0.92 mMol) was suspended in $CH_2Cl_2$ (5 mL) and ethyldiisopropylammine (1.10 mMol, 1.2 Equiv.), t-butoxypirocarbonate (240 mg, 1.10 mMol, 1.2 Equiv.) and DMAP (4-dimethylaminopyridine, 20 mg) were added.

The reaction was stirred 48 h at room temperature and then additionated with the same quantity of reagents and allowed to stay under stirring per other 48 h. The reaction was worked up by dilution with $CH_2Cl_2$ washing with HCl and brine. After drying, 580 mg of 7-Boc-10-deacetylbaccatine III were obtained having the following characteristics: mp 148° C. and 162° C.; 1H-NMR 200 Mhz, $CDCl_3$, TMS as internal standard; Bz δ 8.10, br d, J 8; Bz δ 7.70, br t J 8; Bz δ 7.55, br t J 8; H2, 5.64 d J 7; H10, 5.54, s; H7, 5.36, dd, J 11.0, 8.0; H5, 4.95, d J 8; H13, 4.91, br t, J7.5; H2Oa, 4.32 d, J 8.0; H2Ob 4.26, d, J 8.0; H3, 4.09 d, J 8.8; Ac. 2.29 s; H18 2.09 s; H19 1.83 s; Boc 1.46 s; H16 1.34 s; H17 1.20 s; IR (KBr) 3480 (OH), 1740 (br, C=O), 1603, 1371, 1275, 1259, 1158, 1092, 712.

EXAMPLE 2

Synthesis of 7-BOC-10-deacetylbaccatine III

A 500 mg sample of 10-deacetylbaccatine III (0.92 mMol) was solubilized in 1 ml of dimethylformamide and diluted with 4 ml of $CH_2Cl_2$. The reagents and the reaction conditions are the same of Example I.

EXAMPLE 3

Synthesis of 7-BOC-baccatine III 644 mg (1 mMol) of 7-Boc-10-deacetylbaccatine III prepared according to example 1 or 2 were dissolved in 5 mL of pyridine and at 0° C. under stirring 1.2 g of acetylchloride were added (15 mMol) in 15 h. When the reaction is finished the solution is diluted with $CH_2Cl_2$ under stirring and washed with 60 mL of $H_2O$. The organic phase is washed several times with $H_2O$ and diluted HCl until the elimination of pyridine. The solvent dried on $Na_2SO_4$ is evaporated under vacuum and the residue crystallized from hexane/acetone. 660 mg of 7-Boc-baccatine III were obtained having the following characteristics: mp 190–97° C. 1H-NMR 200 Mhz, $CDCl_3$, TMS as internal standard; Bz 8.10 br d, J 8; Bz 7.70 br t, J 8; Bz δ 7.55, br t J 8; H2, 5.64 d, J 7; H10, 5.52 s; H7, 5.44 dd, J 10.3, 7.0; H5, 4.98, d, J 7.9; H13, 4.50 br t; H2Oa, 4.32 d, J 8.0; H2Ob 4.22 d, J 8.0; H3, 4.02 d, J 6.7; Ac. 2.30 s; H18 2.19 s; Ac. 2.16 s; H19 1.80 s; Boc 1.48 s; H16 1.17 s; H17 1.07 s.

EXAMPLE 4

Synthesis of paclitaxel 1.65 gr of (4S,5R)-2,2-di(chloro methyl)-4-phenyl-N-Benzoyl-5-oxazolidine acid were allowed to react in toluene with 0.69 gr of 7-Boc-baccatine III in the presence of 1.1 Equival. of DCC and 60 mg of 4-dimethylaminopyridine. The reaction mixture was maintained at 60° C. for 12 h under stirring in Argon atmosphere.

At the end of the reaction (TLC) the reaction mixture was filtered form insoluble byproducts and the solvent washed with $H_2O$ and distilled under vacuum. The residue is solubilized in 10 mL of conc. formic acid at 0° C. and kept in this condition for 2 h. The reaction mixture was diluted with 100 mL of $H_2O$ and cloudy solution extracted three times with 50 mL $CH_2Cl_2$. The organic phase was washed with a solution of $NaHCO_3$ and then with $H_2O$. The organic phase after drying on $Na_2SO_4$ is concentrated under vacuum.

The residue was crystallized from ethanol/water and 0.81 gr of paclitaxel having the well known characteristics which have been reported in the literature was obtained.

What is claimed is:

1. A method for the semisynthesis of paclitaxel and analogs of thereof, which comprises:

forming an intermediate compound of formula (II)

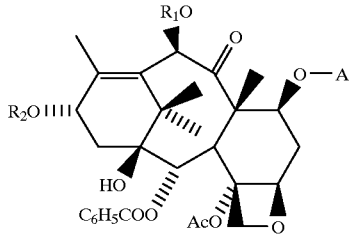

Formula II by protecting with a carbonate compound the hydroxy group at position 7 of 10 deacetylbaccatine III or a similar taxane derivative with the same basic structure wherein:

A is

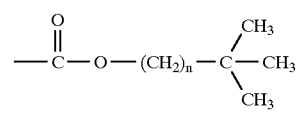

with n being an integer of 0 to 3, $R_1$ is a hydroxy protecting group or a hydrogen atom, and
$R_2$ is a (2R, 3S)-3-phenylisoserine derivative having the structure:

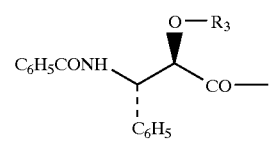

where $R_3$ is a hydroxy protecting group, such as A; a methoxy methyl 1-ethoxyethyl, benzyloxymethyl (β-trialkylsilylethoxy)methyl where each alkyl group contains 1 to 3 carbon atoms, tetrahydropyranyl or 2,2,2-trichloroethoxycarbonyl group; or a hydrogen atom; and removing the A and $R_3$ groups to form paclitaxel or an analog thereof.

2. The method of claim 1 wherein, when n is 0, $R_1$ is an acetyl group, and $R_2$ is a (2R,3S)-3-phenylisoserine derivative having the structure:

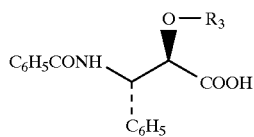

where $R_3$ is a hydrogen atom, the method further comprises:

forming the intermediate compound by reacting 10-deacetylbaccatine III with t-butoxy-pyrocarbonate to obtain 7-t-butoxy-carbonyl-10-deacetyl baccatine III;

acetylating the 10 position of the 7-t-butoxy-carbonyl-10-deacetyl baccatine III to obtain 7-t-butoxy-carbonyl-baccatine III; and esterifying the hydroxy group in position 13 of 7-t-butoxy-carbonyl baccatine III with an oxazolidine derivative of formula (III):

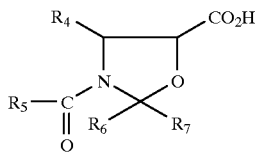

wherein $R_4$ is an aryl group or a straight or branched chain alkyl or alkenyl group having 1–5 carbon atoms; and $R_5$ is $R_4$ or a t-butoxy group, and each of $R_6$ and $R_7$ is a halogenated methyl group.

3. The method of claim 2 wherein $R_4$ is phenyl, $R_5$ is phenyl or a t-butoxy group, and each of $R_6$ and $R_7$ is a $ClCH_2$— or $BrCH_2$— or $F_3C$— group and an excess of the 7-t-butoxycarbonyl baccatine III compound is used relative to the oxazolidine derivative.

4. The method of claim 2 wherein the acetylation is carried out using an acetyl halide or diketene compound.

5. The method of claim 1 wherein the A and $R_3$ groups are selectively removed in mild acidic conditions using a mineral or organic acid.

6. A method for the semisynthesis of paclitaxel, which comprises:

forming an intermediate compound of formula (II)

Formula II

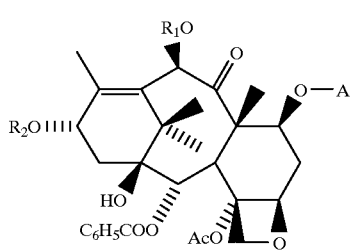

by protecting with a carbonate compound the hydroxy group at position 7 of 10 deacetylbaccatine III or a similar taxane derivative with the same basic structure wherein:

A is

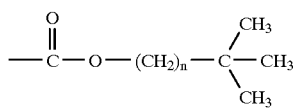

with n being an integer of 0 to 3, $R_1$ is an acetyl group, and $R_2$ is a (2R, 3S)-3-phenylisoserine derivative having the structure:

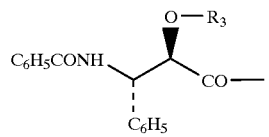

where $R_3$ is a hydroxy protecting group, such as A; a methoxy methyl, 1-ethoxyethyl, benzyloxymethyl, (β-trialkylsilylethoxy)methyl where each alkyl group contains 1 to 3 carbon atoms, tetrahydropyranyl or 2,2,2-trichloroethoxycarbonyl group; or a hydrogen atom; and removing the A and $R_3$ groups to form paclitaxel.

7. The method of claim 6 wherein, $R_1$ is an acetyl group, and $R_2$ is a (2R,3S)-3-phenylisoserine derivative having the structure:

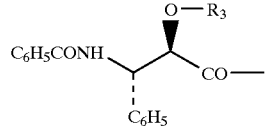

where $R_3$ is a hydrogen atom, the method further comprises:

forming the intermediate compound by reacting 10-deacetylbaccatine III with t-butoxy-pyrocarbonate to obtain 7-t-butoxy-carbonyl-baccatine III;

acetylating the 10 position of the 7-t-butoxy-carbonyl-10-deacetyl baccatine III; and esterifying the hydroxy group in position 13 of 7-t-butoxy-carbonyl baccatine III with an oxazolidine derivative of formula (III):

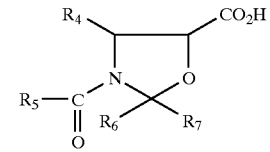

wherein $R_4$ and $R_5$ is an aryl group, and each of $R_6$ and $R_7$ is a halogenated methyl group.

8. The method of claim 7 wherein each of $R_6$ and $R_7$ is a $Cl_2CH_2$— or $BrCH_2$— or $F_3C$— group and an excess of the 7-t-butoxy-carbonyl baccatine III compound is used relative to the oxazolidine derivative.

9. The method of claim 7 wherein the acetylation is carried out using an acetyl halide or a diketene compound.

10. The method of claim 6 wherein the A and $R_3$ groups are selectively removed in mild acidic conditions using a mineral or organic acid.

11. The method of claim 1 wherein A is
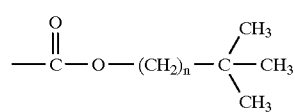
and n is 0.
12. The method of claim 6 wherein A is
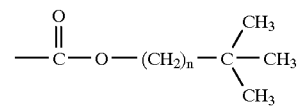
and n is 0.
* * * * *